United States Patent
Nair et al.

(10) Patent No.: US 12,195,793 B2
(45) Date of Patent: Jan. 14, 2025

(54) METHOD OF QUANTIFYING POLYNUCLEOTIDE ANALYTES FROM DRIED SAMPLES

(71) Applicant: Gen-Probe Incorporated, San Diego, CA (US)

(72) Inventors: Sangeetha Vijaysri Nair, San Diego, CA (US); Xianqun Wang, San Marcos, CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 18/733,583

(22) Filed: Jun. 4, 2024

(65) Prior Publication Data

US 2024/0318241 A1    Sep. 26, 2024

Related U.S. Application Data

(62) Division of application No. 17/783,231, filed as application No. PCT/US2020/064004 on Dec. 9, 2020, now Pat. No. 12,037,638.

(60) Provisional application No. 62/946,270, filed on Dec. 10, 2019, provisional application No. 62/945,685, filed on Dec. 9, 2019.

(51) Int. Cl.
| | |
|---|---|
| *G06F 30/20* | (2020.01) |
| *C12Q 1/6865* | (2018.01) |
| *G16B 20/00* | (2019.01) |
| *G16B 40/00* | (2019.01) |
| *C12Q 1/70* | (2006.01) |

(52) U.S. Cl.
CPC ........... *C12Q 1/6865* (2013.01); *G16B 20/00* (2019.02); *G16B 40/00* (2019.02); *C12Q 1/703* (2013.01)

(58) Field of Classification Search
CPC ........ G06B 40/00; G06B 40/22; G16B 20/00; C12Q 1/6865; G06F 30/20
USPC ............................................ 703/2, 19; 435/5
See application file for complete search history.

(56) References Cited

U.S. PATENT DOCUMENTS

| | | | | |
|---|---|---|---|---|
| 7,115,365 B2 * | 10/2006 | Kinjo | ................... | C12Q 1/6851 435/6.12 |
| 2005/0209532 A1 * | 9/2005 | Wandell | ................. | G01N 33/96 600/583 |
| 2006/0286587 A1 * | 12/2006 | Lee | ...................... | C12Q 1/6851 435/6.12 |

(Continued)

FOREIGN PATENT DOCUMENTS

| | | |
|---|---|---|
| WO | 2006052764 A1 | 5/2006 |
| WO | 2016007709 A1 | 1/2016 |

OTHER PUBLICATIONS

Marconi et al. "Evaluation of the Abbott Real-Time HIV-1 quantitative assay with dried blood spot specimens," Clinical Microbiology and Infection, 15(1): 93-97 (2009).

(Continued)

*Primary Examiner* — Andre Pierre Louis
(74) *Attorney, Agent, or Firm* — Michael J. Gilly; Adam M. Breier

(57) ABSTRACT

Presented are methods, systems, and software products useful for determining the concentration of an analyte in a fluid specimen used to produce a dried sample, where the dried sample serves as a source of the analyte in a detection and quantification procedure. Particularly illustrated is the use of dried blood spots for quantifying a polynucleotide analyte.

30 Claims, 1 Drawing Sheet

(56) References Cited

U.S. PATENT DOCUMENTS

2015/0367348 A1* 12/2015 Sano .................... B01L 7/5255
                                                    435/286.1
2019/0369113 A1* 12/2019 Shuford ................ G01N 30/34
2023/0067123 A1   3/2023 Nair et al.

OTHER PUBLICATIONS

Office Action for EP Application No. 20829140.1, dated Mar. 24, 2023, 4 pages.
PCT International Search Report and Written Opinion for PCT/US2020/064004 dated Apr. 6, 2021, 10 pages.
Rouet, et al. "In-house HIV-1 RNA real-time RT-PCR assays: principle, available tests and usefulness in developing countries," Expert Review of Molecular Diagnostics, 8(5): 635-650 (2008).

* cited by examiner

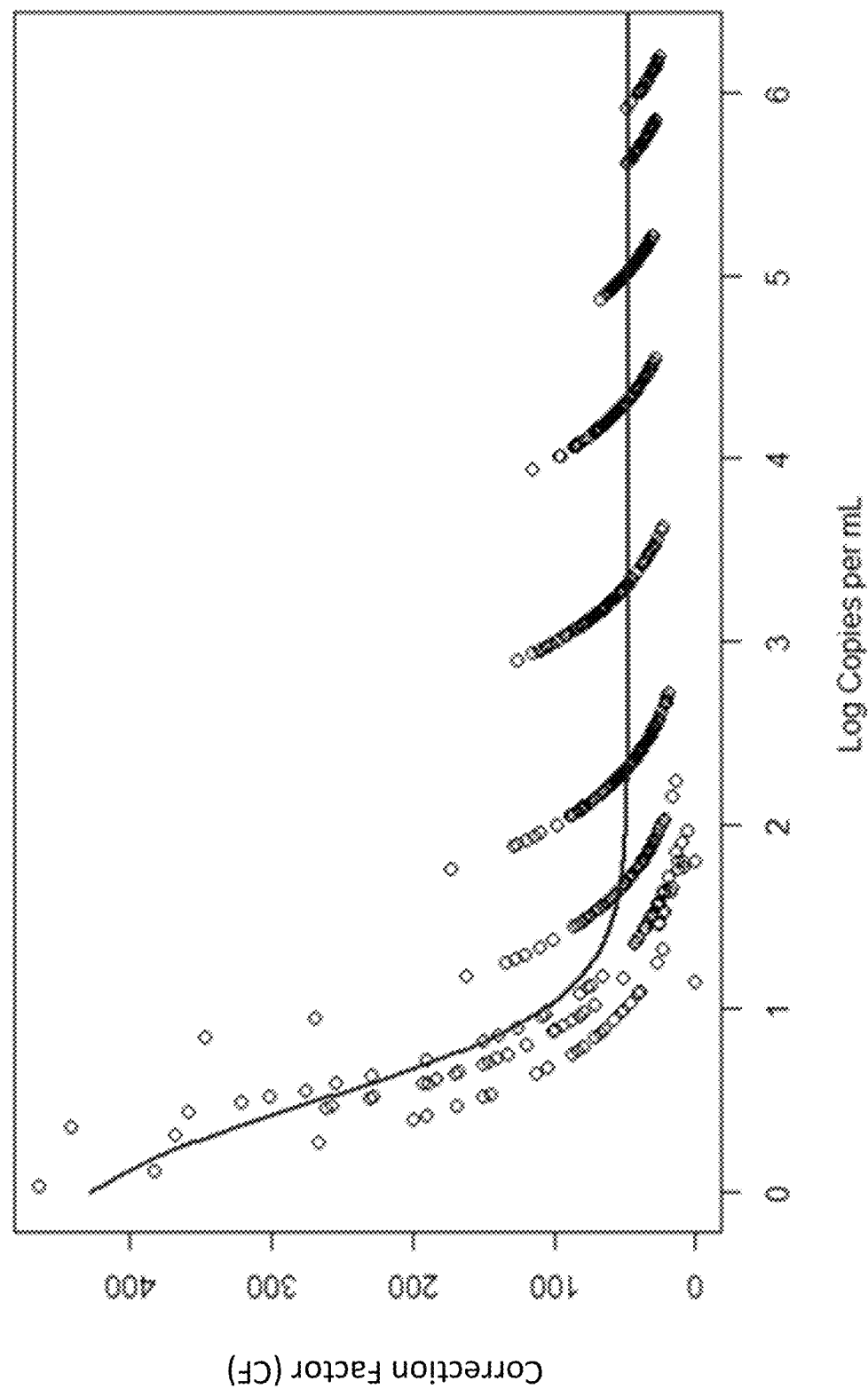

METHOD OF QUANTIFYING POLYNUCLEOTIDE ANALYTES FROM DRIED SAMPLES

CROSS-REFERENCE TO RELATED APPLICATIONS

This application is a divisional application of U.S. application Ser. No. 17/783,231, having a 35 U.S.C. § 371(c) date of Jun. 7, 2022, which is a national phase entry pursuant to 35 U.S.C. § 371 of International Application No. PCT/US2020/064004, filed Dec. 9, 2020, which claims the benefit under 35 U.S.C. § 119(e) of United States Provisional Application Nos. 62/946,270, filed Dec. 10, 2019, and 62/945,685, filed Dec. 9, 2019. The entire disclosures of these earlier applications are hereby incorporated by reference.

TECHNICAL FIELD

The present disclosure generally relates to the field of biotechnology. More specifically, the disclosure concerns methods, systems, and software products for determining the concentration of an analyte in a liquid specimen used for preparing a dried sample, where the dried sample serves as a source of the analyte in a detection and quantification procedure.

BACKGROUND

The use of dried bodily fluid samples, such as dried blood samples, for analyte detection greatly expands the availability of sophisticated laboratory testing by simplifying the requirements for sample collection, transport, and processing. A dried blood spot (DBS) represents a particular type of dried sample. More specifically, a DBS is a form of biosampling where 50-70 μl of blood is blotted onto a circle of filter paper, dried, and then used for detection of one or more bioanalytes in the blood sample. By this approach, a blood spot can be conveniently prepared, dried, and then sent to a remote testing location.

The place where the blood sample is taken for spotting need not have resources for performing conventional blood draws. The advantage here is that bioanalyte testing can be made available to resource-challenged environments, as well as to the anonymous donation and home testing categories.

The use of DBS sampling offers many advantages. For example, samples are easy to collect, store, and transport without requiring refrigeration. Sample acquisition is less invasive than drawing blood by phlebotomy, as only very small blood volumes are required. Dried samples can be stable at ambient temperature for months. Thus, this type of sample provides a convenient way to offer laboratory access to patients outside the traditional clinical setting. The dried sample can even be used as a source of templates for priming in vitro nucleic acid amplification reactions, such as real-time nucleic acid amplification reactions.

Unfortunately, conversion of a quantitative DBS result (e.g., measured in copies/ml using a reconstituted DBS sample) to an accurate "wet sample" result (e.g., measured in copies/ml) for a liquid or fluid sample of a different type (e.g., whole blood or plasma) can be very challenging. Quantitative outputs from nucleic acid analyzers processing liquid samples (e.g., plasma samples) are typically very different from quantitative outputs produced using reconstituted DBS samples. Indeed, efficiencies of sample preparation can differ significantly for direct sampling of a fluid blood product and a reconstituted DBS sample, thereby affecting the quantity of native target entering the pathway for amplification and detection.

A close correspondence between the DBS and wet sample quantitative results can be critical if the DBS result is to be used for making an informed decision regarding a medical treatment, or change in treatment. For example, if DBS test results are to be used for determining failure of an antiretroviral treatment for HIV-1, then according to World Health Organization guidelines (WHO Consolidated Guidelines on the use of antiretroviral drugs for treating or preventing HIV infection, 2016) the test must be capable of detecting when the HIV viral load exceeds a level of 1,000 copies/ml in plasma.

The present disclosure addresses the need for converting results from DBS testing to a wet sample standard, thereby relating the two results to each other in a manner that is both highly accurate and precise.

SUMMARY OF THE DISCLOSURE

Provided herein are the following embodiments.

Embodiment 1 is a method of quantifying a polynucleotide analyte present in a fluid blood sample that dried to produce a dried blood spot (DBS), the method comprising the steps of: (a) performing a nucleic acid amplification reaction using the DBS as a source of templates to produce amplification products and obtain a measured result, the measured result indicating a concentration or an amount of the polynucleotide analyte; and (b) multiplying the measured result by a correction factor to obtain a corrected result, wherein the correction factor is the solution to an equation that specifies the correction factor as a function of the measured result, thereby quantifying the polynucleotide analyte present in the fluid blood sample.

Embodiment 2 is a method of quantifying a polynucleotide analyte present in a fluid blood sample that created a dried blood spot (DBS), the method comprising the steps of: (a) performing a nucleic acid amplification reaction using the DBS as a source of templates to produce amplification products and obtain a measured result, the measured result indicating a concentration or an amount of the polynucleotide analyte; (b) solving an equation to determine a correction factor, wherein the equation specifies the correction factor as a function of the measured result; and (c) multiplying the measured result by the correction factor to obtain a corrected result, thereby quantifying the polynucleotide analyte present in the fluid blood sample.

Embodiment 3 is the method of either embodiment 1 or 2, wherein the equation in step (b) comprises a non-linear equation.

Embodiment 4 is the method of embodiment 3, wherein the non-linear equation comprises coefficients optimized in a mathematical curve fitting procedure to define a fitted curve.

Embodiment 5 is the method of embodiment 4, wherein the non-linear equation comprises four coefficients.

Embodiment 6 is the method of any one of embodiments 1 to 5, wherein step (a) comprises performing with an automated nucleic acid analyzer that amplifies the polynucleotide analyte and detects amplification products as the nucleic acid amplification reaction is occurring.

Embodiment 7 is the method of embodiment 6, wherein the equation in step (b) is a non-linear equation prepared using results obtained from an automated nucleic acid analyzer different from the automated nucleic acid analyzer used for performing the nucleic acid amplification reaction in step (a).

Embodiment 8 is the method of any one of embodiments 1 to 5, wherein step (a) comprises performing with an automated nucleic acid analyzer that isolates the polynucleotide analyte, and then amplifies the isolated polynucleotide analyte.

Embodiment 9 is the method of embodiment 8, wherein the automated nucleic acid analyzer further detects synthesis of amplification products as the nucleic acid amplification reaction is occurring.

Embodiment 10 is the method of any one of embodiments 1 to 9, wherein the measured result indicates a concentration of the polynucleotide analyte in a plasma sample.

Embodiment 11 is the method of any one of embodiments 1 to 10, wherein the nucleic acid amplification reaction is an isothermal nucleic acid amplification reaction.

Embodiment 12 is the method of embodiment 11, wherein the isothermal nucleic acid amplification reaction is a transcription-associated nucleic acid amplification reaction.

Embodiment 13 is the method of embodiment 12, wherein the transcription-associated nucleic acid amplification reaction comprises a transcription mediated amplification (TMA) reaction.

Embodiment 14 is the method of any one of embodiments 1 to 13, wherein the polynucleotide analyte comprises a segment of a viral genome.

Embodiment 15 is the method of embodiment 14, wherein the viral genome comprises RNA.

Embodiment 16 is the method of any one of embodiments 1 to 15, wherein the polynucleotide analyte comprises a segment of an HIV-1 genome.

Embodiment 17 is the method of any one of embodiments 1 to 16, wherein the fluid blood sample comprises whole blood.

Embodiment 18 is a computer programmed with software instructions for quantifying a polynucleotide analyte present in a fluid blood sample that dried to produce a dried blood spot (DBS), the software instructions, when executed by the computer, cause the computer to: (a) receive a measured result; (b) solve an equation to determine a correction factor, wherein the equation specifies the correction factor as a function of the measured result; (c) multiply the measured result by the correction factor to calculate a corrected result; and (d) record the corrected result in a non-transient form, thereby quantifying the polynucleotide analyte.

Embodiment 19 is the computer of embodiment 18, wherein the measured result is determined from results of a real-time nucleic acid amplification reaction, wherein the real-time nucleic acid amplification reaction is carried out using the DBS as a source of templates to produce amplification products, and wherein the measured result indicates a concentration or an amount of the polynucleotide analyte.

Embodiment 20 is the computer of either embodiment 18 or 19, wherein the measured result and the corrected result are both expressed in concentration units.

Embodiment 21 is the computer of any one of embodiments 18 to 20, wherein the equation is a non-linear equation.

Embodiment 22 is the computer of embodiment 21, wherein the non-linear equation comprises coefficients optimized in a mathematical curve fitting procedure to define a fitted curve.

Embodiment 23 is the computer of embodiment 22, wherein the non-linear equation comprises four coefficients.

Embodiment 24 is the computer of any one of embodiments 18 to 23, wherein the non-transient form comprises storage on a computer-readable memory device.

Embodiment 25 is the computer of any one of embodiments 18 to 24, wherein the fluid blood sample comprises whole blood.

Embodiment 26 is a computer-readable storage medium comprising instructions which, when executed by a computer, cause the computer to carry out the method of embodiment 18.

Embodiment 27 is a system for quantifying a polynucleotide analyte that may be present in a test sample, comprising: a nucleic acid analyzer comprising a temperature-controlled incubator; a fluorometer in optical communication with the temperature-controlled incubator, wherein the fluorometer is configured to measure production of nucleic acid amplification products contained within the temperature-controlled incubator as a function of time or cycle number; and a computer in communication with the fluorometer, wherein the computer is programmed with software instructions causing the computer to: (a) calculate a measured result using measurements made by the fluorometer, (b) solve an equation to determine a correction factor, wherein the equation specifies the correction factor as a function of the measured result; (c) multiply the measured result by the correction factor to calculate a corrected result, and (d) record the corrected result in a non-transient form, thereby quantifying the target polynucleotide analyte present in the test sample.

Embodiment 28 is the system of embodiment 27, wherein the temperature-controlled incubator is configured to maintain a constant temperature.

Embodiment 29 is the system of embodiment 27, wherein the temperature-controlled incubator is configured for temperature cycling.

Embodiment 30 is the system of any one of embodiments 27 to 29, wherein the fluorometer is configured for detecting a plurality of different wavelengths of light.

Embodiment 31 is the system of any one of embodiments 27 to 30, wherein the temperature-controlled incubator, the fluorometer, and the computer are all integral components of the nucleic acid analyzer.

Embodiment 32 is the system of any one of embodiments 27 to 31, wherein the measured result comprises a concentration value for the polynucleotide analyte.

Embodiment 33 is a method of quantifying an analyte present in a bodily fluid sample that dried to produce a dried sample, the method comprising the steps of: (a) performing a reaction using the dried sample as a source of analyte to obtain a measured result, the measured result indicating a concentration or an amount of the analyte; and (b) multiplying the measured result by a correction factor to obtain a corrected result, wherein the correction factor is the solution to an equation that specifies the correction factor as a function of the measured result, thereby quantifying the analyte present in the bodily fluid sample.

Embodiment 34 is the method of embodiment 33, wherein the equation in step (b) comprises a non-linear equation.

Embodiment 35 is the method of embodiment 34, wherein the non-linear equation comprises coefficients optimized in a mathematical curve fitting procedure to define a fitted curve.

Embodiment 36 is the method of embodiment 35, wherein the non-linear equation comprises four coefficients.

Embodiment 37 is the method of any one of embodiments 33 to 36, wherein the analyte is a polynucleotide analyte, and wherein step (a) comprises performing with an automated nucleic acid analyzer that amplifies the polynucleotide analyte and detects amplification products as the nucleic acid amplification reaction is occurring.

Embodiment 38 is the method of either embodiment 33 or 37, wherein the equation in step (b) comprises a non-linear equation, wherein the non-linear equation comprises coefficients optimized in a mathematical curve fitting procedure to define a fitted curve, and wherein the non-linear equation is prepared using results obtained from an automated nucleic acid analyzer different from the automated nucleic acid analyzer used for performing the nucleic acid amplification reaction in step (a).

Embodiment 39 is the method of embodiment 37, wherein step (a) comprises performing with an automated nucleic acid analyzer that isolates the polynucleotide analyte, and then amplifies the isolated polynucleotide analyte.

Embodiment 40 is the method of embodiment 39, wherein the automated nucleic acid analyzer further detects synthesis of amplification products as the nucleic acid amplification reaction is occurring.

Embodiment 41 is the method of any one of embodiments 37, 39 or 40, wherein the measured result indicates a concentration of the polynucleotide analyte in a plasma sample.

Embodiment 42 is the method of any one of embodiments 37 to 41, wherein the nucleic acid amplification reaction is an isothermal nucleic acid amplification reaction.

Embodiment 43 is the method of embodiment 42, wherein the isothermal nucleic acid amplification reaction is a transcription-associated nucleic acid amplification reaction.

Embodiment 44 is the method of embodiment 43, wherein the transcription-associated nucleic acid amplification reaction comprises a transcription mediated amplification (TMA) reaction.

Embodiment 45 is the method of any one of embodiments 37 to 44, wherein the polynucleotide analyte comprises a segment of a viral genome.

Embodiment 46 is the method of embodiment 45, wherein the viral genome comprises RNA.

Embodiment 47 is the method of any one of embodiments 37 to 46, wherein the polynucleotide analyte comprises a segment of an HIV-1 genome.

Embodiment 48 is the method of any one of embodiments 33 to 47, wherein the bodily fluid sample is selected from the group consisting of a whole blood sample, a plasma sample, a urine sample, and a saliva sample.

DETAILED DESCRIPTION

Introduction and Overview

Disclosed herein is an approach for accurately converting a quantitative result obtained using a dried bodily fluid sample to a corresponding result, measured in concentration units, for a liquid sample that was used to create the dried sample. HIV nucleic acids served as the model analyte in the exemplary procedures. There is no need to modify the chemistries used for nucleic acid amplification and detection to achieve outstanding results. This means that a single assay chemistry can be used to quantify a polynucleotide analyte using either liquid samples or reconstituted dry samples over a wide dynamic range. Dried blood spot sampling was used to illustrate the technique.

Rather than modifying assay chemistry, a numerical "correction factor" (hereafter CF) multiplier is used to achieve the desired results. The CF can be multiplied by the outputted or "measured" result of a quantitative assay using a reconstituted DBS as the source of analyte. This converts the measured result to a corresponding concentration (e.g., copies/ml) of a different sample type. For example, a result obtained using a reconstituted DBS sample can be converted or adjusted to a corresponding concentration in a whole blood sample. Thus, a single assay chemistry (e.g., a single type of amplification and detection reaction mixture, or a single type of assay kit) can now be used for amplifying and quantifying the polynucleotide analyte, regardless of the sample type (e.g., whole blood, plasma, reconstituted DBS, etc.).

A key feature of the present technique involves the manner in which the CF is determined. It was discovered during development of the technique that the required CF is not constant over the quantitative dynamic range of the assay. Instead, the CF varies as a function of the output of a nucleic acid analyzer calibrated using a liquid sample (e.g., where the output can be measured in concentration units). As the amount of analyte present in a dried sample (e.g., a DBS) undergoing reconstitution and testing decreases, the CF required for accurate quantitation increases.

In some embodiments, the CF to be used as a numerical multiplier is calculated using an equation fitted to a collection of data. In some embodiments, the equation is a non-linear equation. In other embodiments, the equation can include one or more linear equations. The data used to obtain a fitted equation represent calculated correction factors as a function of the quantitative output value delivered from a nucleic acid analyzer calibrated for processing liquid samples (e.g., plasma). In some embodiments, the fitted equation used for determining the CF to be used on one instrument can be determined on that same instrument. However, it is more convenient, and so preferable, to determine the fitted equation using one or more instruments, and then to use that fitted equation on a different instrument (i.e., an instrument that was not used for determining the fitted equation). For example, the fitted equation can be prepared by the manufacturer of an assay kit, and then transferred to and used by a customer or end-user on a different instrument (sometimes referred to as a "local" instrument).

In some embodiments, the CF is calculated from a plurality of fitted curves or lines, where the curve or line appropriate for CF determination depends on the output of the analyzer prior to applying the CF multiplier. Again, the CF is chosen as a function of the measured concentration or amount of analyte indicated to be present when testing the dried sample (e.g., a DBS sample) after reconstitution. The chosen CF is then multiplied by that measured concentration to yield an adjusted quantitative result that quantifies the analyte.

Definitions

The following terms have the indicated meanings in the specification unless expressly indicated to have a different meaning.

The terms "a," "an," and "the" include plural referents, unless the context clearly indicates otherwise. For example, "a polynucleotide" as used herein is understood to represent one or more polynucleotides. As such, the terms "a" (or "an"), "one or more," and "at least one" can be used interchangeably herein.

As used herein, a "dried bodily fluid sample" is a sample of a bodily fluid, such as a sample of whole blood or other blood product, where the water component of the fluid has been substantially removed. Typically, the bodily fluid will be applied to a solid matrix (e.g., a filter paper, a glass fiber filter, a fabric, a flocked swab, a sponge material, etc.) prior to removal of the water component.

As used herein, a "dried blood spot" (sometimes "DBS") refers to a sample of blood or blood product that is dried prior to analysis for the presence or amount of an analyte. Preferably, the sample of blood is applied to a solid matrix and then permitted to dry to create or produce the DBS. In some embodiments, the solid matrix is a filter, such as a paper filter or a glass fiber filter, a fabric, a flocked swab, or a sponge material. Preferably, the DBS includes a sample of dried whole blood. Preferred analytes for testing using DBS samples include polynucleotide analytes.

As used herein, a "reconstituted" sample is a liquid or fluid sample resulting from combining a dried biological sample (e.g., a DBS) with a liquid (e.g., an extraction solution) that dissolves, liquifies, or resuspends the dried biological sample. In some embodiments, the reconstituted sample results from combining or contacting a dried blood spot on a solid support matrix (e.g., a filter paper "card") with an extraction buffer, which may include a pH buffer and a detergent. Thus, the dried blood spot can serve as a source of analyte (e.g., polynucleotide analyte) to be detected when analyte of the reconstituted sample is used for detection. In some embodiments, procedures for detecting polynucleotide analytes of a reconstituted sample may involve in vitro nucleic acid amplification procedures.

As used herein, "polynucleotide" means either RNA, DNA, or a chimeric molecule containing both RNA and DNA. The term also embraces molecules containing nucleotide analogs of RNA or DNA.

As used herein, a "test sample" is any sample to be investigated for the presence of a particular polynucleotide sequence. Test samples include any polynucleotide-containing material obtained from a human, animal, environmental, or laboratory-derived or synthetic sample. Preferred test samples include bodily fluid samples. Whole blood, plasma, and serum are particularly preferred examples of test samples. Other test samples include saliva, urine, etc.

As used herein, an "analyte" is a chemical or biochemical species that is to be detected and/or quantified. For example, a "polynucleotide analyte" refers to a polynucleotide (e.g., a segment of an HIV-1 polynucleotide) that is to be detected or quantified in a test procedure.

As used herein, a "nucleic acid analyzer" (or "polynucleotide analyzer") is an apparatus that amplifies, detects, and quantifies polynucleotide analytes. Certain preferred nucleic acid analyzers include a temperature-controlled incubator (e.g., a block, plate, or chamber), a fluorometer in optical communication with contents of the temperature-controlled incubator, and one or more computers or processors that process data gathered by the fluorometer to quantify a polynucleotide analyte of interest.

By "analyte polynucleotide standard" is meant a composition comprising a known quantity of a polynucleotide analyte, or fragment thereof. For example, an HIV-1 analyte polynucleotide standard may contain a known number of copies of an HIV-1 genome, HIV-1 transcript, or in vitro synthesized transcript representing a portion of the viral genome. A "WHO" standard (e.g., HIV-1 WHO standard) is an analyte polynucleotide standard of established concentration that is provided by the World Health Organization.

By "calibration standard" is meant a composition that includes a known or predetermined amount analyte polynucleotide standard in combination with a known constant amount of an internal calibrator polynucleotide. Two different calibration standards can contain different amounts of polynucleotide analyte or a fragment thereof, but will contain the same amount of internal calibrator polynucleotide. The polynucleotide analyte of the analyte polynucleotide standard, and the internal calibrator polynucleotide will be distinguishable from each other, for example by having nucleotide base sequences that are different. A test instrument (e.g., a nucleic acid analyzer) is said to be "calibrated" when a calibration standard has been used to ensure the instrument delivers accurate results. For example, an instrument may be calibrated to deliver accurate results when processing plasma samples.

An "amplicon" (sometimes "amplification product") is a polynucleotide product of an amplification reaction, wherein a target polynucleotide sequence of a polynucleotide analyte served as the template for synthesis of polynucleotide copies or amplification products.

By "amplification" or "nucleic acid amplification" or "polynucleotide amplification" and the like is meant any known procedure for obtaining multiple copies, allowing for RNA and DNA equivalents, of a target polynucleotide sequence or its complement or fragments thereof. Amplification of "fragments thereof" refers to production of an amplified nucleic acid (i.e., polynucleotide) containing less than the complete target region nucleic acid sequence or its complement. Such fragments may be produced by amplifying a portion of the target nucleic acid, for example, by using an amplification oligonucleotide that hybridizes to, and initiates polymerization from, an internal position of the target polynucleotide.

As used herein, the terms "coamplify" and "coamplifying" and variants thereof refer to a process wherein different target polynucleotide sequences are amplified in a single (i.e., the same) amplification reaction. For example, a polynucleotide analyte and an unrelated internal calibrator polynucleotide are "coamplified" when both polynucleotides are amplified in reactions taking place in a single tube, and when both amplification reactions share at least one reagent (e.g., deoxyribonucleotide triphosphates, enzyme, primer(s), etc.) in common.

As used herein, "thermal cycling" refers to repeated changes of temperature, (i.e., increases or decreases of temperature) in a reaction mixture. Samples undergoing thermal cycling may shift from one temperature to another, stabilize at that temperature, transition to a second temperature or return to the starting temperature. The temperature cycle may be repeated as many times as required to study or complete the particular chemical reaction of interest.

By "target" or "target nucleic acid" or "target polynucleotide" is meant a polynucleotide containing a sequence that is to be amplified, detected and quantified. A target polynucleotide sequence that is to be amplified preferably will be positioned between two oppositely disposed oligonucleotides, and will include the portion of the target polynucleotide that is complementary to each of the oligonucleotides.

By "target polynucleotide sequence" or "target sequence" or "target region" is meant a specific deoxyribonucleotide or ribonucleotide sequence comprising all or part of the nucleotide sequence of a single-stranded polynucleotide molecule, and the deoxyribonucleotide or ribonucleotide sequence complementary thereto.

By "transcription-associated amplification" is meant any type of polynucleotide amplification that uses an RNA polymerase to produce multiple RNA transcripts from a polynucleotide template. Conventionally, these amplification reactions employ at least one primer having a 3'-end that can be extended by the activity of a DNA polymerase.

One example of a transcription-associated amplification method, called "Transcription Mediated Amplification" (TMA), generally employs an RNA polymerase, a DNA polymerase, deoxyribonucleoside triphosphates, ribonucleoside triphosphates, and a promoter-containing oligonucleotide complementary to the target polynucleotide.

Variations of TMA are well known in the art as disclosed in detail in Burg et al., U.S. Pat. No. 5,437,990; Kacian et al., U.S. Pat. Nos. 5,399,491 and 5,554,516; Kacian et al., PCT No. WO 93/22461; Gingeras et al., PCT No. WO 88/01302; Gingeras et al., PCT No. WO 88/10315; Malek et al., U.S. Pat. No. 5,130,238; Urdea et al., U.S. Pat. Nos. 4,868,105 and 5,124,246; McDonough et al., PCT No. WO 94/03472; and Ryder et al., PCT No. WO 95/03430. Other transcription-associated amplification methods employing only a single primer that can be extended by a DNA polymerase, as disclosed in the U.S. Pat. No. 7,374,885 are particularly embraced by the definition and are highly preferred for use in connection with the method disclosed herein.

As used herein, an "oligonucleotide" or "oligomer" is a polymeric chain of at least two, generally between about five and about 100, chemical subunits, each subunit comprising a nucleotide base moiety, a sugar moiety, and a linking moiety that joins the subunits in a linear spatial configuration. Common nucleotide base moieties are guanine (G), adenine (A), cytosine (C), thymine (T) and uracil (U), although other rare or modified nucleotide bases able to hydrogen bond are well known to those skilled in the art. Oligonucleotides may optionally include analogs of any of the sugar moieties, the base moieties, and the backbone constituents. Preferred oligonucleotides of the present invention fall in a size range of about 10 to about 100 residues. Oligonucleotides may be purified from naturally occurring sources, but preferably are synthesized using any of a variety of well-known enzymatic or chemical methods.

By "amplification oligonucleotide" or "amplification oligomer" is meant an oligomer that hybridizes to a target polynucleotide, or its complement, and participates in a polynucleotide amplification reaction. Examples of amplification oligomers include primers that contain a 3'-end that is extended as part of the amplification process, but also include oligomers that are not extended by a polymerase (e.g., a 3'-blocked oligomer) but may participate in, or facilitate efficient amplification from a primer. Preferred size ranges for amplification oligomers include those that are about 10 to about 80 nucleotides long, or 10 to about 60 nucleotides long and contain at least about 10 contiguous bases, and more preferably at least 12 contiguous bases that are complementary to a region of the target polynucleotide sequence (or a complementary strand thereof). The contiguous bases are preferably at least about 80%, more preferably at least about 90%, and most preferably about 100% complementary to the target sequence to which amplification oligomer binds. An amplification oligomer may optionally include modified nucleotides or analogs, or additional nucleotides that participate in an amplification reaction but are not complementary to or contained in the target polynucleotide. An amplification oligomer that is 3'-blocked but capable of hybridizing to a target polynucleotide and providing an upstream promoter sequence that serves to initiate transcription is referred to as a "promoter provider" oligomer.

A "primer" is an amplification oligomer that hybridizes to a template polynucleotide and has a 3'-OH end that can be extended by a DNA polymerase. The 5' region of the primer may be non-complementary to the target polynucleotide (e.g., a promoter sequence), resulting in an oligomer referred to as a "promoter-primer." Those skilled in the art will appreciate that any oligomer that can function as a primer can be modified to include a 5' promoter sequence, and thus could function as a promoter-primer. Similarly, any promoter-primer can be modified by removal of, or synthesis without, a promoter sequence and still function as a primer.

As used herein, a "probe" is an oligonucleotide that hybridizes specifically to a target sequence in a polynucleotide, preferably in an amplified polynucleotide, under conditions that promote hybridization, to form a detectable hybrid. Certain preferred probes include a detectable label (e.g., a fluorescent label or chemiluminescent label).

As used herein, "time-dependent" monitoring of polynucleotide amplification, or monitoring of polynucleotide amplification in "real-time" refers to a process wherein the amount of amplicon present in a polynucleotide amplification reaction is measured as a function of reaction time or cycle number, and then used to determine a starting amount of template that was present in the reaction mixture at the time the amplification reaction was initiated. For example, the amount of amplicon can be measured prior to commencing each complete cycle of an amplification reaction that comprises thermal cycling, such as PCR. Alternatively, isothermal amplification reactions that do not require physical intervention to initiate the transitions between amplification cycles can be monitored continuously, or at regular time intervals to obtain information regarding the amount of amplicon present as a function of time.

As used herein, a "growth curve" refers to the characteristic pattern of appearance of a synthetic product, such as an amplicon, in a reaction as a function of time or cycle number. A growth curve is conveniently represented as a two-dimensional plot of time or cycle number (x-axis) against some indicator of product amount, such as a fluorescence measurement (y-axis). Some, but not all, growth curves have a sigmoid-shape.

As used herein, the "baseline phase" of a growth curve refers to the initial phase of the curve wherein the amount of product (such as an amplicon) increases at a substantially constant rate, this rate being less than the rate of increase characteristic of the growth phase (which may have a log-linear profile) of the growth curve. The baseline phase of a growth curve typically has a very shallow slope, frequently approximating zero.

As used herein, the "growth phase" of a growth curve refers to the portion of the curve wherein the measurable product substantially increases with time. Transition from the baseline phase into the growth phase in a typical polynucleotide amplification reaction is characterized by the appearance of amplicon at a rate that increases with time.

Transition from the growth phase to the plateau phase of the growth curve begins at an inflection point where the rate of amplicon appearance begins to decrease.

As used herein, the "plateau phase" of a triphasic growth curve refers to the final phase of the curve. In the plateau phase, the rate of measurable product formation generally is substantially lower than the rate of amplicon production in the log-linear phase, and may even approach zero.

As used herein, the phrase "indicia of amplification" refers to features of real-time run curves which indicate a predetermined level of progress in polynucleotide amplification reactions. Such indicia are commonly determined by mathematical analysis of run curves, sometimes referred to as "growth curves," which display a measurable signal (such as a fluorescence reading) whose intensity is related to the quantity of an amplicon present in a reaction mixture as a function of time, cycle number, etc.

As used herein, the phrase "threshold-based indicia of amplification" refers to indicia of amplification that measure the time or cycle number when a growth curve signal crosses an arbitrary value or threshold. TTime determinations are examples of threshold-based indicia of amplification, while TArc and OTArc determinations are examples of non-threshold-based indicia of amplification.

As used herein, the phrase "time-dependent" indicia of amplification refers generally to indicia of amplification (e.g., a reaction progress parameter) that are measured in time units (e.g., minutes). Time-dependent indicia of amplification are commonly used for monitoring progress in isothermal polynucleotide amplification reactions that are not characterized by distinct "cycles." All of TTime, TArc and OTArc are examples of time-dependent indicia of amplification.

As used herein, an "internal calibrator" (sometimes "IC" herein) is a polynucleotide that can be amplified in an in vitro polynucleotide amplification reaction, and that is distinguishable from a polynucleotide analyte that coamplified in the same reaction. "Internal" means that the calibrator polynucleotide is amplified, detected and quantified within the same reaction mixture as the polynucleotide analyte, or fragment thereof. Generally speaking, the amount or concentration of the internal calibrator will be constant in different reactions used for preparing calibration curves, and for quantifying the polynucleotide analyte. Preferably, the constant amount or concentration of internal calibrator will be a known amount of internal calibrator, or a known concentration of internal calibrator. In certain preferred embodiments, the internal calibrator and the polynucleotide analyte are coamplified in an in vitro polynucleotide amplification reaction using one or more different amplification oligomers or primers. For example, the analyte and internal calibrator polynucleotides employed in the working Examples detailed below were amplified using amplification oligonucleotides that were not shared. In other preferred embodiments, the internal calibrator and the polynucleotide analyte are coamplified in an in vitro polynucleotide amplification reaction using one or more identical amplification oligomers or primers.

As used herein, the phrase "as a function of" describes the relationship between a dependent variable (i.e., a variable that depends on one or more other variables) and an independent variable (i.e., a variable that may have its value freely chosen without considering the values of any other variables), wherein each input value for the independent variable relates to exactly one output value for the dependent variable.

Conventional notation for an equation that relates a y-value (i.e., the dependent variable) "as a function of" an x-value (i.e., the independent variable) is $y=f(x)$.

As used herein, a "computer" is an electronic device capable of receiving and processing input information to generate an output. The computer may be a standalone device (e.g., a personal computer), or may be an integrated component of an instrument (e.g., a nucleic acid analyzer that amplifies a polynucleotide target and monitors synthesis of amplification products as a function of reaction cycle number or time). Particularly embraced by the term is an embedded processor resident within an analyzer instrument, and harboring embedded software instructions (sometimes referred to a "firmware").

As used herein, "optimizing" or "fitting" an equation refers to a process, as commonly practiced in mathematical modeling or curve fitting procedures, for obtaining numerical values for coefficients in an equation to yield an expression that "fits" or approximates experimental measurements. Typically, an optimized equation will define a best-fit curve.

As used herein, the terms "optimized equation," and "fitted equation" are alternative references to an equation containing fixed numerical values for coefficients as the result of an optimizing procedure. "Fitted" curves result from optimizing an equation.

By "local" is meant relating to an end-user. For example, a local instrument refers to an end-user's instrument. A local calibration plot refers to a calibration plot using results obtained by an end-user, for example by conducting an amplification reaction on the local instrument.

By "kit" is meant a packaged combination of materials, typically intended for use in conjunction with each other. Kits in accordance with the invention may include instructions or other information in a "tangible" form (e.g., printed information, electronically recorded on a computer-readable medium, or otherwise recorded on a machine-readable medium such as a bar code for storing numerical values).

By "consisting essentially of" is meant that additional component(s), composition(s) or method step(s) that do not materially change the basic and novel characteristics of the present invention may be included in the present invention. Any component(s), composition(s), or method step(s) that have a material effect on the basic and novel characteristics of the present invention would fall outside of this term.

BRIEF DESCRIPTION OF THE DRAWINGS

FIG. 1 is a plot of calculated correction factor (CF) values (vertical axis) as a function of the "observed" or "measured" concentration (measured in copies/ml) of an HIV-1 polynucleotide analyte (horizontal axis). Open circular data points represent calculated CF values at different measured target concentrations in a procedure that amplified polynucleotide analyte from reconstituted DBS samples. A solid curve has been fitted to the collected data points by mathematically optimizing a 4-PL equation.

DESCRIPTIONS OF CERTAIN EMBODIMENTS

The presently disclosed technique was demonstrated using the Aptima™ HIV-1 Quant Dx assay from Hologic, Inc., (Marlborough, MA) as a model system. This viral load monitoring assay is both highly sensitive and specific, and can be used to assess responses to antiretroviral treatment by monitoring changes in the concentration of HIV-1 RNA. The assay is an in vitro polynucleotide amplification test for the detection and quantification of human immunodeficiency virus type 1 (HIV-1) RNA groups M, N, and O that can be performed on the fully automated Panther™ system (Hologic, Inc.). The system running the viral load assay is calibrated to output a concentration of virus, measured in copies/ml using a 500 µl test sample. For example, the model assay can be used for monitoring the effect of antiviral treatment by measuring changes in the concentration of HIV-1 RNA in plasma. There would be a benefit for accurately correlating quantitative results obtained using DBS samples and plasma samples using the same calibration as well as reagents, and protocol for target capture, amplification and detection.

The model assay involves three main steps, which all take place in a single tube on the automated Panther system for polynucleotide analysis: target capture, target amplification by Transcription Mediated Amplification, and detection of the amplification products (amplicon) by the fluorescently labeled hybridization probes (torches). During target capture, the specimen is treated with a detergent to solubilize the viral envelope, denature proteins, and release viral genomic RNA. Capture oligonucleotides hybridize to highly conserved regions of the HIV-1 genome, if present, in the test sample. The hybridized target is then captured onto magnetic microparticles that are separated from the specimen in a magnetic field. Wash steps remove extraneous components from the reaction tube. Target amplification then occurs via TMA, which is a transcription-mediated polynucleotide amplification method that utilizes two enzymes, MMLV (Moloney murine leukemia virus) reverse transcriptase and T7 RNA polymerase. The reverse transcriptase is used to generate a DNA copy (containing a promoter sequence for T7 RNA polymerase) of the target sequence. T7 RNA polymerase produces multiple copies of RNA amplicon from the DNA copy template. The model assay utilizes the TMA method to amplify two regions of HIV-1 RNA (pol and LTR). Amplification of these specific regions is achieved using specific primers which are designed to amplify HIV-1 groups M, N, and O. The primer design and dual target approach ensure accurate detection and quantitation of HIV-1. Detection is achieved using single-stranded polynucleotide torches that are present during the amplification of the target and that hybridize specifically to the amplicon in real-time. Each torch has a fluorophore and a quencher. When the torch is not hybridized to the amplicon, the quencher is in close proximity to the fluorophore, and so suppresses fluorescence. When the torch binds to the amplicon, the quencher is moved farther away from the fluorophore and emits a signal at a specific wavelength when excited by a light source. A higher fluorescent signal is generated as more torches hybridize to amplicon. The time taken for the fluorescent signal to reach a specified threshold is proportional to the starting HIV-1 concentration. Each reaction has an internal calibrator/internal control (IC) that coamplifies with the HIV-1 analyte and controls for variations in specimen processing, amplification, and detection. The concentration of a sample is determined by the Panther system software using the HIV-1 and IC signals for each reaction and comparing them to calibration information. Determined concentrations are calibrated for HIV-1 in plasma samples, and not for reconstituted DBS samples. The determined concentration here can alternatively be referred to as an "observed" result or a "measured" result.

There are different types of DBS, and each can be used for performing the quantitative technique described herein. Blood samples can be obtained from infants using standard heal stick or finger stick techniques. Here the skin surface of the infant is disinfected and then pricked with a sterile needle or lancet. Next, 3-5 drops of blood can be added to each of a plurality (e.g., 5) of spots on a DBS "card," ensuring that the entire surface of the circle is completely filled. The finger stick technique also can be used with adults to obtain DBS samples. Whole blood conveniently may be stored for up to 24 hours at 2° C. to 30° C. prior to application to the DBS cards. In this instance, 70 µl of stored whole blood can be applied to the center of a filter circle on a DBS card, for example using a calibrated 200 µl pipette. Spotted blood samples, however obtained, can be dried at ambient temperature for 4-24 hours. Individual cards harboring the dried samples can be placed into an envelope (e.g., a glassine envelope) for storage or transport. Multiple glassine envelopes can be packaged into a resealable plastic bag with one or more desiccant packs. However they are packaged, DBS samples can be held or shipped at ambient temperatures for subsequent processing.

Preferred Polynucleotide Amplification Methods

Examples of in vitro polynucleotide amplification methods useful in connection with the present technique include, but are not limited to: Transcription Mediated Amplification (TMA), Single-Primer Nucleic Acid Amplification, Nucleic Acid Sequence-Based Amplification (NASBA), the Polymerase Chain Reaction (PCR), Strand Displacement Amplification (SDA), Self-Sustained Sequence Replication (3SR), DNA Ligase Chain Reaction (LCR) and amplification methods using self-replicating polynucleotide molecules and replication enzymes such as MDV-1 RNA and Q-beta enzyme. Methods for carrying out these various amplification techniques respectively can be found in U.S. Pat. No. 5,399,491, U.S. patent application Ser. No. 11/213,519, published European patent application EP 0 525 882, U.S. Pat. Nos. 4,965,188, 5,455,166, Guatelli et al., *Proc. Natl. Acad. Sci. USA* 87:1874-1878 (1990), International Publication No. WO 89/09835, U.S. Pat. No. 5,472,840 and Lizardi et al., *Trends Biotechnol.* 9:53-58 (1991). The disclosures of these documents which describe how to perform polynucleotide amplification reactions are hereby incorporated by reference. Thus, although the model system used for demonstrating the correction factor adjustment technique employed TMA as the amplification reaction mechanism, alternative amplification reaction mechanisms also can be used with equally good results.

Examples of Preferred Real-Time Quantitative Techniques

Generally speaking, real-time polynucleotide amplification and detection procedures involve monitoring production of amplification reaction products as the amplification reaction is occurring. As indicated above, any number of different amplification methods can be used to create amplification products. In some embodiments, synthesis of amplification products as a function of time or cycle number is indicated by detection of a fluorescent signal generated in the amplification reaction mixture. Examples of methods useful for calibrating instruments carrying out real-time amplification reactions are given in U.S. Pat. Nos. 9,932,628 and 9,976,175, the disclosures of these patents being incorporated by reference herein for all purposes. Success of these methods is independent of the manner in which run curves in the real-time procedures are obtained. Stated differently, different indicia of amplification can be used to establish when an amplification reaction has achieved a desired threshold level of amplification progress.

A variety of indicia of amplification can be used for quantifying analytes before the CF adjustment is applied to the data. Real-time amplification and detection for quantifying polynucleotide analytes is highly preferred for use in connection with the disclosed CF adjustment technique, and is subject to alternative data processing procedures with good results in each case. For example, mathematical and computing techniques that will be familiar to those having an ordinary level of skill in the art can be used to identify the time of occurrence of the maximum of the first derivative, or the time of occurrence of the maximum of the second derivative of a real-time run curve. Approaches for determining these features of a growth curve have been detailed by Wittwer et al., in U.S. Pat. No. 6,503,720, the disclosure of which is incorporated by reference herein. Other useful approaches involve calculating a derivative of a growth curve, identifying a characteristic of the growth curve, and then determining the threshold time or cycle number corresponding to the characteristic of the derivative. Such techniques have been disclosed in U.S. Pat. No. 6,783,934, the disclosure of which is incorporated by reference. Still other useful indicia of amplification include "TTime" and "TArc." Different approaches for determining TArc values employ directionally similar vectors (i.e., resulting in a value identified simply by "TArc"), and directionally opposed vectors (i.e., resulting in a value identified as "OTArc"). Still other techniques involve identifying cycle threshold (e.g., "Ct")

values as the time or cycle number during a reaction at which a signal, preferably a fluorescent signal, equals a static threshold (e.g., a predetermined static threshold value).

Preferred Systems and Apparatus

The methods disclosed herein are conveniently implemented using a computer or similar processing device ("computer" hereafter). In different preferred embodiments, software or machine-executable instructions for performing an algorithm can be loaded or otherwise held in a memory component of a freestanding computer, or in a memory component of a computer linked to a device used for monitoring, preferably as a function of time, the amount of a product undergoing analysis. In a highly preferred embodiment, software for executing the correction factor adjustment procedure is held in a memory component of a computer that is linked to, or that is an integral part of a device capable of monitoring the amount of an amplicon present in a reaction mixture as a function of time. This includes a processing device component on an electronic circuit board (e.g., embedded software) of an automated nucleic acid analyzer.

In some embodiments, the computer can be in communication with, either by wired or wireless means, a fluorometer that detects fluorescent signals, where the fluorometer is arranged or configured to monitor fluorescent signals generated in one or more reaction vessels contained within a temperature-controlled incubator. The incubator can be a temperature-controlled block (e.g., a metal block configured for receiving and containing one or more tubes, or even a multi-well plate), or a chamber that exposes one or more reaction vessels to controlled temperature conditions.

In some embodiments, either or both of a controller system for controlling a real-time amplification device and/or the detection system of the real-time amplification device can be coupled to an appropriately programmed computer which functions to instruct the operation of these instruments in accordance with preprogrammed or user input instructions. The computer preferably also can receive data and information from these instruments, and interpret, manipulate and report this information to the user.

In some embodiments, the computer also can include appropriate software for receiving user instructions, either in the form of user input into a set of parameter fields, or in the form of preprogrammed instructions (e.g., preprogrammed for a variety of different specific operations). The software then converts these instructions to appropriate language for instructing the operation of the real-time amplification controller to carry out the desired operation. Preferably, the computer also is capable of receiving data from one or more sensors/detectors included within the system, and interprets the data in accordance with the programming. The system preferably includes software that correlates a feature of a growth curve representing the quantity of amplified copies of the polynucleotide of interest as a function of time, as detected by the detector, to the number of copies of the polynucleotide of interest present in a test sample.

Preferably, when the computer used for executing the disclosed CF determination and adjustment procedure is an integral component of an apparatus for performing and analyzing real-time polynucleotide amplification reactions, the apparatus preferably comprises a temperature-controlled incubator, a detection device for collecting signals (e.g., a fluorometer), and an analyzing device (e.g., a computer or processor) for analyzing signals. The apparatus optionally can further include an output device for displaying data obtained or generated. The analyzing device may be connected to the temperature-controlled incubator through an input device known in the art, and/or connected to an output device known in the art for data display. In one embodiment, the temperature-controlled incubator is capable of temperature cycling.

Generally speaking, the various components of an apparatus for performing the real-time polynucleotide amplification useful in connection with the disclosed methods will be conventional components that will be familiar to those having an ordinary level of skill in the art. The temperature-controlled incubator used to perform and analyze real-time polynucleotide amplification may be of a conventional design which can hold a plurality of reaction tubes, or reaction samples in a temperature-controlled block in standard amplification reaction tubes or in wells of a multiwell plate. In one aspect, the detection system is suitable for detecting optical signals from one or more fluorescent labels. The output of the detection system (e.g., signals corresponding to those generated during the amplification reaction) can be fed to the computer for data storage and manipulation. In one embodiment, the system detects multiple different types of optical signals, such as multiple different types of fluorescent labels and has the capabilities of a microplate fluorescence reader. The detection system is preferably a multiplexed fluorimeter containing an excitation light source, which may be a visible light laser or an ultraviolet lamp or a halogen lamp, a multiplexer device for distributing the excitation light to the individual reaction tubes and for receiving fluorescent light from the reaction tubes, a filtering means for separating the fluorescence light from the excitation light by their wavelengths, and a detection means for measuring the fluorescence light intensity. Preferably, the detection system of the temperature-controlled incubator provides a broad detection range that allows flexibility of fluorophore choice, high sensitivity and excellent signal-to-noise ratio. Optical signals received by the detection system are generally converted into signals which can be operated on by the processor to provide data which can be viewed by a user on a display of a user device in communication with the processor. The user device may comprise a user interface or may be a conventional commercially available computer system with a keyboard and video monitor. Examples of data which can be displayed by the user device include amplification plots, scatter plots, sample value screens for all the tubes or reaction vessels in the assembly and for all labels used, an optical signal intensity screen (e.g., fluorescent signal intensity screen), final call results, text reports, and the like.

Computer Program Products

Included within the scope of the invention are software-based products (e.g., tangible embodiments of software for instructing a computer to execute various procedural steps) that can be used for performing the data processing method. These include software instructions stored on computer-readable media, such as magnetic media, optical media, "flash" memory devices, and computer networks or cloud storage. As well, the invention embraces a system or an apparatus that amplifies polynucleotides, detects polynucleotide amplification products, and processes results to indicate a quantitative result for target in a test sample. Although the various components of the apparatus preferably function in a cooperative fashion, there is no requirement for the components to be part of an integrated assembly (e.g., on a single chassis). However, in a preferred embodiment, components of the apparatus are connected together. Included within the meaning of "connected" are connections via wired and wireless connections.

Particularly falling within the scope of the invention is an apparatus or system that includes a computer linked to a device that amplifies polynucleotides and monitors amplicon synthesis as a function of cycle number or time, where the computer is programmed to execute the quantitative algorithm disclosed herein. An exemplary system in accordance with the invention will include a temperature-controlled incubator, and a fluorometer capable of monitoring and distinguishing at least two wavelengths of fluorescent emissions. These emissions may be used to indicate target amplicon synthesis, and IC amplicon synthesis.

In connection with computer-implemented or software-implemented embodiments of the disclosure, a result can be recorded or stored in a "non-transient" format where it can be accessed for reference at a later time than when the data analysis to be recorded was carried out or performed. For example, a computed result can be recorded in a non-transient format by printing on paper, or by storing on a computer-readable memory device (e.g., a hard drive, flash memory device, file in cloud storage, etc.).

Curve Fitting Procedures

In accordance with the disclosed method of creating a curve, plot, or fitted equation for determining correction factors, the relating procedure or step preferably involves obtaining one or more equations optimized to fit a data set. The data set comprises calculated CF values as a function of a result produced by a nucleic acid analyzer calibrated for determining the amount of analyte in a known volume of liquid sample. This can be accomplished by applying standard mathematical curve fitting techniques to each of the data sets to result in a fitted equation that defines a curve associated therewith. In some embodiments, one or more linear equations can be used for determining an appropriate CF from the output of a nucleic acid analyzer calibrated to deliver quantitative results for samples of a type (e.g., plasma samples) other than a reconstituted DBS sample. In other embodiments, the equation used in the curve fitting procedure preferably is a non-linear equation that contains no less than two, more preferably no less than three, and more preferably no less than four coefficients that can be optimized or determined during the curve fitting procedure. Some highly preferred equations have exactly four coefficients, while other highly preferred equations have exactly five coefficients. Optimizing an equation to fit the measured indicia of amplification can easily be accomplished using a commercially available software package, such as the SOLVER program which is available as an EXCEL add-in tool for finding an optimal value for a formula, and equation solving from Microsoft Corporation (Redmond, WA). Certain curves generated by this procedure can be shaped such that increasing levels of the polynucleotide analyte input into a reaction correlate with reduced CF values.

Although other equations can be used in the curve fitting procedure, the methods described below employed a four-parameter logistic (4-PL) equation having the following form:

$$CF = c + \frac{d - c}{(1 + \exp^{\wedge}(b*(x - e)))} \quad \text{(Eq 1)}$$

In this equation, the CF dependent variable represents the correction factor as a function of the observed or measured concentration (x) in logarithmic scale of the polynucleotide analyte. Again, the "observed" or "measured" concentration is the quantitative output of an assay calibrated for detecting the HIV-1 polynucleotide analyte in a test sample, but need not be calibrated for quantifying the analyte in a reconstituted DBS sample. The four coefficients in the equation that can be optimized by standard procedures are identified as b to e. The "exp" constant is the base of the natural logarithm (i.e., about 2.7183). Of course, it is to be understood that success in using the present invention does not require the use of any particular equation.

Alternative Equations for Performing Curve Fitting

Notably, although a 4-PL equation was used for illustrating the disclosed technique, other mathematical functions can also be used in the procedure to simulate the trend of CF values versus measured outputs.

Those having an ordinary level of skill in the art will appreciate that numerous types of equations may be used in the procedures disclosed herein. Examples of symmetric transition functions include, but are not limited to: Sigmoid, Gaussian Cumulative, Lorentzian Cumulative and Cumulative Symmetric Double Sigmoidal. Examples of asymmetric transition functions include, but are not limited to: Logistic Dose Response (LDR), Log Normal Cumulative, Extreme Value Cumulative, Pulse Cumulative, Pulse Cumulative with Power Term, Weibull Cumulative, Asymmetric Sigmoid, Asymmetric Sigmoid Reverse Asymmetry, Cascade Formation, and Cumulative Exponentially Modified Gaussian. Additionally, simple linear and non-linear equations, such as multiple order polynomials, power, exponential and logarithmic functions can be used to model real-time data with subsequent adjustment of the baseline coefficient, as detailed herein. Kinetic functions with baseline coefficients can also be used in the same manner. Exemplary basic kinetic equations containing baseline coefficients include but are not limited to: Half Order Decay and Formation, First Order Decay and Formation, Second Order Decay and Formation, Second Order Decay and Formation (Hyperbolic Forms), and Third Order Decay and Formation, Variable Order Decay and Formation. Exemplary complex kinetic equations containing baseline coefficients include but are not limited to: Simultaneous First and Second Order Decay and Formation, First Order Sequential Formation, Two Component First Order Decay, Two First Order Independent Decay and Formation, Two Second Order Independent Decay and Formation, and First and Second Order Independent Decay and Formation. Exemplary kinetic equilibrium equations containing baseline coefficients include but are not limited to: Simple Equilibrium (Forward and Reverse Rate), Simple Equilibrium (Net Rate and Equilibrium Concentration), Complex Equilibrium A=B+C, and Complex Equilibrium A+B=C+D. Exemplary intermediate kinetic equations containing baseline coefficients include but are not limited to: First Order Intermediate and First Order Intermediate with Equilibrium. One of ordinary skill in the art will readily understand that success of the disclosed CF adjustment method does not depend on the use of any particular equation for performing the curve fitting step. Indeed, it is believed that any equation having coefficients that can be optimized in a curve fitting procedure for the disclosed CF adjustment procedures.

All of the above-listed equation types can be used to carry out the disclosed methods. This is because success of the procedure depends not on the particular equation used, but on its ability to fit the data optimally.

WORKING EXAMPLES

As stated above, the disclosed technique improved the quantitative capacity of assays carried out using dried bodily fluid samples by delivering reliable results that correlated with concentrations of polynucleotide analyte in the starting sample that was used to create the dry sample. The Examples presented below are intended to be illustrative, and are not intended to limit the disclosure in any way.

Those having an ordinary level of skill in the art will appreciate that the lower limit of quantification ("LLOQ") in an assay is the lowest concentration of an analyte that can be quantified with a certain level of accuracy and precision, and have at least 95% reactivity. Likewise, those having an ordinary level of skill in the art will appreciate that the limit of detection ("LOD") in an assay is the lowest concentration of analyte that can be consistently detected in at least 95% of tested samples.

The LLOQ of an assay is the minimum concentration at which the following two requirements are met: (1) reactivity should be at least 95%; and (2) total error (TE) should meet specifications for assay accuracy. In the case of the model viral load assay used for illustrating the present CF adjustment technique, the TE specification is ≤1 log accuracy at the LLOQ. Two different "total error" assessment approaches were used to gauge the impacts of different correction factor approaches at the lower limit of quantification (LLOQ). These approaches were the CLSI EP-17-A2 guideline recommended Westgard, and the root mean square (RMS) models for calculation of LLOQ. The procedure involved determining accuracy and precision of quantification at low HIV concentrations using reconstituted DBS samples as the source of analyte. Stocks of a diluted WHO HIV standard having an assigned concentration value, which served as the "gold standard" for quantification, were used to create DBS samples. More particularly, various amounts of HIV WHO standard stock were spiked into different aliquots of whole blood, and the resulting dilutions used to prepare DBS samples.

In accordance with the above-cited Westgard model, the TE can be calculated using the following equation.

$$\text{Bias} + (2 \times \text{Std Dev}) \le 1 \log \quad (\text{Eq 2})$$

In accordance with the above-cited RMS model, the TE can be calculated using the following equation.

$$\sqrt{(\text{Bias})^2 + (\text{StdDev})^2} \le 1 \log \quad (\text{Eq 3})$$

In the context of these equations, "bias" is the difference between the expected (i.e., actual) and the "recovered" assay result. As used herein, a "recovered" result has been adjusted using a CF multiplier, and so differs from a measured result, which has not been adjusted using a CF multiplier. Simply stated, a recovered result can be calculated by multiplying a measured result by a CF. The CF adjustment is able to improve assay quantification at low analyte concentrations by reducing bias (improving accuracy) and improving precision (by reducing Std. Dev.).

An initial approach to improve DBS quantification involved the use of static (i.e., constant) CF value multipliers. More specifically, pre-selected constants in the range of from 15 to 33 were multiplied by the measured value of a real-time polynucleotide amplification assay that was calibrated to deliver quantitative results for a 500 μl liquid sample (e.g., plasma). It is important for assays that measure HIV viral load to meet accuracy goals at concentrations ≤1,000 copies/ml. This is because the WHO recommended medical decision point for monitoring effectiveness of antiretroviral treatment is 1,000 copies/ml. Therefore, clinical sensitivity and specificity of the assay was calculated at the medical decision point of 1,000 copies/ml using recovered assay results for DBS calculated using different static CFs. No significant difference in assay sensitivity or specificity was seen when CFs ranging from 25 to 33 were used. According to one approach, the LOD determined for reconstituted DBS samples (i.e., 873 copies/ml) was divided by the LLOQ for plasma samples (i.e., 30 copies/ml) for the same assay chemistry to establish a constant CF value of 29.1 for use as a multiplier. Thus, an assay conducted using a 500 μl aliquot of a reconstituted DBS sample (e.g., a filter having been spotted with 70 μl of whole blood and then dried, and subsequently reconstituted with 1 ml of buffer) that yielded a "measured" or observed output of 35 copies/ml would be multiplied by 29.1 to give a corrected (i.e., "recovered") result of 1,019 copies/ml.

Example 1 describes a real-time polynucleotide amplification assay that quantified HIV-1 polynucleotides using reconstituted DBS samples. The automated nucleic acid analyzer used in the procedure was calibrated to deliver results measured in copies/ml for plasma samples.

Example 1

Static Correction Factor Quantifies Polynucleotide Analyte with Excessive Error

DBS samples harboring known quantities of HIV-1 polynucleotides were prepared using laboratory procedures that will be familiar to those having an ordinary level of skill in the art. Whole blood was spiked with HIV-1 from the value assigned WHO standard virus stock to produce samples having concentrations in the range of from 50 copies/ml to 1,200 copies/ml. Whole blood samples (70 μl each) of the different HIV concentrations were separately applied to standard filter paper cards, and then allowed to dry. Dried blood spots were punched from the cards and each DBS was combined with 1 ml of a buffered detergent solution (i.e., DBS extraction buffer). One-half of each sample (500 μl) was then used for testing in the Aptima HIV-1 Quant Dx real-time viral load assay on the Panther automated nucleic acid analyzer (Hologic, Inc.; Marlborough, MA). At least 90 replicates of DBS samples tested using different HIV-1 reagent lots on the platform yielded essentially equivalent outcomes. Table 1 presents illustrative results obtained using one of the reagent lots. Columns 1 and 2 list the actual stock concentrations of analyte in whole blood that were used for creating the DBS samples. Column 3 ("Reactivity") indicates the percentage of trials yielding positive results (i.e., HIV-1 analyte detected). Column 4 ("Avg. Recovered") indicates the averaged product of multiplying the static CF by the measured concentration of analyte outputted by the automated analyzer. Column 5 ("Bias") indicates the magnitude of deviation of the average recovered concentration result from the actual analyte concentration. Column 6 ("Std Dev Log Copies") indicates the standard deviation among recovered results presented in column 4. Column 7 ("Total Error (Westgard)") presents results calculated in accordance with a standard Westgard analysis protocol. Column 8 ("Total Error (RMS)") presents results calculated in accordance with the above-cited RMS analysis protocol.

TABLE 1

Quantitative Adjustment Using a Static CF

| Target (copies/ml) | Log Target (copies/ml) | Reactivity | Avg. Recovered (log copies/ml) | Bias | Std Dev Log Copies | Total Error (Westgard) | Total Error (RMS) |
|---|---|---|---|---|---|---|---|
| 900 | 2.95 | 97% | 2.02 | 0.93 | 0.53 | 2.00 | 1.07 |
| 1,000 | 3.00 | 97% | 2.00 | 1.00 | 0.52 | 2.04 | 1.13 |
| 1,200 | 3.08 | 97% | 2.21 | 0.87 | 0.53 | 1.92 | 1.01 |

The results presented in Table 1 indicated that Total Error, regardless of the method used for making the determination, undesirably exceeded the acceptable 1.0 threshold goal. Although not shown, different constant CF values substituted in place of 29.1 also gave unacceptable results.

Example 2 presents experimental results showing that a single (i.e., constant) CF cannot be used for quantifying analyte over the dynamic range of the assay, particularly at lower analyte concentrations. As will be apparent from the results presented below, lower concentration values outputted by the nucleic acid analyzer calibrated for processing plasma samples had to be multiplied by higher CFs to recover correct starting concentrations used to prepare the DBS samples. Likewise, higher outputted values had to be multiplied by lower CFs to recover correct starting concentrations used to prepare the DBS samples.

Example 2

The Correction Factor is not Constant Across the Dynamic Range of the Quantitative Real-Time Assay Procedures essentially described under Example 1 were followed to prepare DBS samples using whole blood spiked with different levels of the HIV-1 analyte. The DBS samples were processed as described above, and eluted polynucleotides amplified and detected using the Aptima HIV-1 Quant Dx real-time viral load assay on the automated Panther nucleic acid analyzer (Hologic, Inc.). The target HIV-1 concentration used for DBS preparation was compared to measured concentration in the assay to calculate the appropriate CF for each HIV-1 concentration input according to equation Eq 4.

$$CF = \frac{\text{Analyte concentration in blood used to prepare the } DBS}{\text{Concentration result measured by nucleic acid analyzer}} \quad (\text{Eq 4})$$

TABLE 2

Correction Factor Needed for Adjustment Varies as a Function of Measured Target Concentration

| Target (log copies/ml) | Target (copies/ml) | Measured Conc. (copies/ml) | Calculated CF (Eq 4) |
|---|---|---|---|
| 2.70 | 500 | 1.1 | 455 |
| 2.88 | 750 | 4.0 | 188 |
| 3.00 | 1,000 | 28 | 36 |
| 3.38 | 2,400 | 33 | 73 |
| 4.00 | 10,000 | 175 | 57 |
| 5.00 | 100,000 | 1,546 | 65 |
| 6.00 | 1,000,000 | 27,347 | 37 |
| 6.70 | 5,011,872 | 122,119 | 41 |
| 7.30 | 19,952,623 | 543,574 | 37 |
| 7.60 | 39,810,717 | 1,229,821 | 32 |

The results presented in Table 2 clearly indicated that a single, fixed or static CF value could not be used for correctly quantifying polynucleotide analyte over the dynamic range of the assay. The final column in the table generally reveals a trend where higher CF values were required for correctly quantifying samples having lower concentrations of the polynucleotide analyte.

Example 3 describes development of a quantitative approach using a CF value that varied as a function of the measured result calibrated for a liquid sample (e.g., plasma) different from the liquid sample undergoing testing (i.e., an extracted DBS sample). This type of variable CF is sometimes referred to as "non-static."

Example 3

Development of a Non-Static Correction Factor

A total of 747 DBS samples were prepared using whole blood stocks having different known analyte HIV-1 concentrations that spanned the quantification range of the model real-time quantitative assay. For completeness, the known analyte HIV-1 concentrations used for creating the DBS samples were the same as presented in the first column of Table 2. The DBS samples were reconstituted with 1 ml of a buffered detergent solution (i.e., DBS extraction buffer), and 500 µl of the resulting solution was used for nucleic acid isolation and target amplification and detection with the model real-time quantitative assay. Target (i.e., actual) HIV-1 concentration was compared to measured concentration in the assay to calculate the appropriate CF for each HIV-1 concentration using equation Eq 4. The CF multiplier required for adjusting HIV-1 measured analyte concentration values to equal known input analyte concentrations were then plotted as a function of measured copy values. The resulting data was then used for optimizing a non-linear equation according to standard mathematical curve-fitting techniques that will be familiar to those having an ordinary level of skill in the art. Although many different non-linear equations can be used for this purpose, the technique is illustrated in FIG. 1 using a fitted 4-PL equation. It will be recognized that curve-fitting using 4-PL equations are frequently used for processing data exhibiting biphasic or sigmoid curve properties.

The results presented in FIG. 1 graphically confirmed that the CF values were not static or constant, but instead varied as a non-linear function of the measured concentration value outputted by the nucleic acid analyzer calibrated for processing of plasma samples. Clusters of data points appearing as spaced-apart crescent-shapes demonstrate variability among calculated CF results for single-level input amounts. Stated differently, a collection of DBS samples harboring substantially the same amount of polynucleotide analyte (i.e., the dried blood spots having been prepared using a single stock of diluted analyte) naturally yielded a range of CF values. Coefficients for the optimized 4-PL equation (i.e., Eq 1) shown as the fitted curve in FIG. 1 were as follows: b=3.705178; c=47.21279; d=486.6657; and e=0.506889. Notably, the fact that the data in the present case did not particularly conform to a sigmoid shape did not prevent usefulness of the 4-PL equation, as demonstrated in the following Example.

Example 4 demonstrates use of CF values determined by a fitted non-linear curve. More specifically, the determined CF value was multiplied by the measured quantitative result outputted from a real-time nucleic acid analyzer (measured in copies/ml) to indicate the analyte concentration in the liquid sample used to prepare the dried blood spot.

Example 4

Correction Factor Calculated from Non-Linear Curve Fit Improved Analyte Quantification Procedures essentially described under Example 1 were followed to prepare DBS samples using whole blood spiked with different levels of the HIV-1 analyte. The DBS samples were processed as described above, and eluted polynucleotides amplified and detected using the Aptima HIV-1 Quant Dx real-time viral load assay on the Panther automated nucleic acid analyzer. Outputted (i.e., measured) quantitative results were multiplied by CF values taken from the fitted curve shown in FIG. 1. More specifically, the equation for the fitted curve shown in the figure was solved to determine a CF value using the outputted quantitative result on the horizontal axis as the independent variable (i.e., x-value) in the equation. The determined CF value was then multiplied by the same outputted quantitative result (i.e., x-value) to calculate a "recovered" (i.e., adjusted) concentration. Results are presented in Table 3.

TABLE 3

Quantitative Adjustment Using a Calculated CF

| Target (copies/ml) | Target (log copies/ml) | Reactivity | Recovered (log copies/ml) | Bias | Std Dev Log Copies | Total Error (Westgard) | Total Error (RMS) |
| --- | --- | --- | --- | --- | --- | --- | --- |
| 900 | 2.95 | 97% | 2.79 | 0.17 | 0.47 | 1.10 | 0.50 |
| 1,000 | 3.00 | 97% | 2.78 | 0.22 | 0.46 | 1.15 | 0.51 |
| 1,200 | 3.08 | 97% | 2.91 | 0.17 | 0.37 | 0.91 | 0.41 |

The results presented in Table 3 confirmed that use of the CF calculated from the fitted non-linear equation substantially improved the quantitative capacity of the assay. As indicated under the final two columns of the table, TE values were substantially reduced when compared with results presented in Table 1. Stated differently, use of the CF calculated from a fitted non-linear equation yielded significant improvements when compared with a similar process employing a fixed value (i.e., CF=29.1). The LLOQ of the assay in this Example was 813 copies/ml (i.e., 2.91 log copies/ml). Among all results obtained using three different reagent lots, the highest LLOQ determined using calculated CF values taken from the fitted curve shown in FIG. 1 was 883 copies/ml (i.e., 2.95 log copies/ml).

Example 5

Use of Correction Factor Equation Improves Assay Precision and Accuracy

Procedures disclosed herein were used to prepare DBS samples from whole blood stocks spiked with an HIV-1 analyte at 900 copies/ml, 1,000 copies/ml, or 1,200 copies/ml. Polynucleotides eluted from the samples were amplified using the Aptima HIV-1 Quant DX real-time viral load assay on the Panther automated nucleic acid analyzer. Reported results were obtained using procedures carried out in our own laboratories with the intention of analyzing performance around the medically relevant decision point of 1,000 copies/ml. Averaged results obtained using three different reagent lots are presented in Table 4.

TABLE 4

Use of the CF Equation Increased Accuracy and Precision

| Target Conc (copies/ml) | Log Target Conc (copies/ml) | Avg. Adjusted HIV log copies/ml using CF of 29.1 | Avg. Adjusted HIV log copies/ml using CF Equation | Precision Std. Dev. Log copies/ml for CF of 29.1 | Precision Std. Dev. Log copies/ml for CF Equation |
| --- | --- | --- | --- | --- | --- |
| 900 | 2.95 | 2.21 | 2.89 | 0.48 | 0.42 |
| 1,000 | 3.00 | 2.18 | 2.91 | 0.49 | 0.32 |
| 1,200 | 3.08 | 2.38 | 3.01 | 0.46 | 0.27 |

The results presented in Table 4 show that the CF calculated from the nonlinear equation, when multiplied by the result measured in copies/ml for a plasma sample, advantageously yielded higher accuracy in quantitative assignments with greater precision. Columns 1 and 2 in the table indicate HIV-1 target concentrations of stock samples used to create the DBS samples. Columns 3 and 4 show adjusted HIV concentrations determined by multiplying a CF (29.1 for column 3; calculated value using the equation from the fitted curve in FIG. 1 for column 4) by an outputted result from the model viral load assay that had been calibrated for quantifying plasma samples, and not DBS samples. The difference between the values presented under column 2 and the values presented under columns 3 and 4 reflect accuracy of assays employing the different correction factor approaches. In every instance, the magnitude of the difference was lower when the CF equation was used instead of the static CF. These smaller differences indicate more accurate quantification. Columns 5 and 6 show measures of precision (i.e., standard deviations among measured concentrations for replicates). Again, in every instance the standard deviation was lower when the CF equation was used instead of the static CF. This indicated use of the CF equation was associated with greater precision in the quantitative results.

Example 5 presents clinical data demonstrating how improved assay quantification resulting in higher clinical sensitivity at the medical decision point of 1,000 copies/ml for HIV-1 was achieved by employing a CF multiplier calculated using an equation for the fitted curve shown in FIG. 1. Notably, the data used to obtain the fitted curve was not the same clinical data that was processed in the Example. This further demonstrated how a fitted curve (or the equation therefor) could be prepared using one data set, and then used for determining CF values and processing a different data set (e.g., a data set obtained using a different instrument to perform the assay).

Example 5

Improvement in Clinical Performance at the WHO Recommended Medical Decision Point of 1,000 Copies/ml for HIV-1 Viral Load Monitoring Paired plasma and DBS specimens were collected from HIV-1 positive patients on antiretroviral therapy. Two replicates were tested for the plasma specimen, and viral load results obtained using the procedures described herein were then averaged and used as a reference. Approximately 5 reconstituted DBS samples were also tested from each patient, and the measured quantitative results multiplied either by a static CF (i.e., 29.1) or a CF calculated using the non-linear equation for the fitted curve shown in FIG. 1 to obtain recovered concentration values. Results were then compared to the plasma reference standard at the medically relevant decision point of 1,000 copies/ml. It should be noted that 90% of results in this study had plasma viral load <10,000 copies/ml, making this dataset ideal for assessment of clinical performance around 1,000 copies/ml of HIV.

As supported by the results presented in Tables 5 and 6, assay sensitivity at 1,000 copies/ml improved from 79.83% to 90.56% when the CF was determined from the non-linear equation compared to the static value. The change from one CF value to the other did not have a significant negative impact on specificity. This will be evident from the specificity of 94.30% obtained using the static CF of 29.1 versus 91.36% obtained using the CF equation. The close correspondence between these latter values indicated minimal impact on specificity.

TABLE 5

Results Processed Using a Static Correction Factor

| HIV DBS viral load in copies/ml | HIV viral load in copies/ml plasma (2 replicate average) | | |
|---|---|---|---|
| (CF 29.1) | <1,000 | >1,000 | Grand Total |
| <1,000 | 1,157 | 47 | 1,204 |
| >1,000 | 70 | 186 | 256 |
| Grand Total | 1,227 | 233 | 1,460 |
| Total Agreement | 91.99% | | |
| Sensitivity (Pos Agreement) | 79.83% | | |
| Specificity (Neg Agreement) | 94.30% | | |

TABLE 6

Results Processed Using a Correction Factor Calculated from a Non-Linear Equation

| HIV DBS viral load in copies/ml | HIV viral load in copies/ml plasma (2 replicate average) | | |
|---|---|---|---|
| (CF Equation) | <1,000 | >1,000 | Grand Total |
| <1,000 | 1,121 | 22 | 1,143 |
| >1,000 | 106 | 211 | 317 |
| Grand Total | 1,227 | 233 | 1,460 |
| Total Agreement | 91.23% | | |
| Sensitivity (Pos Agreement) | 90.56% | | |
| Specificity (Neg Agreement) | 91.36% | | |

While the present disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the disclosure requires features or combinations of features other than those expressly recited in the claims. Accordingly, the present disclosure is deemed to include all modifications and variations encompassed within the spirit and scope of the following numbered embodiments.

Although various embodiments of the present disclosure have been illustrated and described in detail, it will be readily apparent to those skilled in the art that various modifications may be made without departing from the present disclosure or from the scope of the appended claims.

What is claimed is:

1. A method of quantifying a polynucleotide analyte present in a fluid blood sample that dried to produce a dried blood spot (DBS), the method comprising the steps of:
    (a) performing a nucleic acid amplification reaction using the DBS as a source of templates to produce amplification products and obtain a measured result, the measured result A indicating a concentration or an amount of the polynucleotide analyte;
    (b) multiplying the measured result by a correction factor to obtain a corrected result,
        wherein the correction factor is the solution to an equation that specifies the correction factor as a function of the measured result, and
        wherein the equation comprises a non-linear equation, and (c) quantifying the polynucleotide analyte present in the fluid blood sample and recording the corrected result.

2. A method of quantifying a polynucleotide analyte present in a fluid blood sample that created a dried blood spot (DBS), the method comprising the steps of:
    (a) performing a nucleic acid amplification reaction using the DBS as a source of templates to produce amplification products and obtain a measured result, the measured result indicating a concentration or an amount of the polynucleotide analyte;
    (b) solving an equation to determine a correction factor, wherein the equation specifies the correction factor as a function of the measured result, and
        wherein the equation comprises a non-linear equation;
    (c) multiplying the measured result by the correction factor to obtain a corrected result,
    and (d) quantifying the polynucleotide analyte present in the fluid blood sample and recording the corrected result.

3. The method of claim 2, wherein the non-linear equation comprises coefficients optimized in a mathematical curve fitting procedure to define a fitted curve.

4. The method of claim 3, wherein the non-linear equation comprises four coefficients.

5. The method of claim 2, wherein step (a) comprises performing with an automated nucleic acid analyzer that amplifies the polynucleotide analyte and detects amplification products as the nucleic acid amplification reaction is occurring.

6. The method of claim 5, wherein the non-linear equation in step (b) is a non-linear equation prepared using results obtained from an automated nucleic acid analyzer different from the automated nucleic acid analyzer used for performing the nucleic acid amplification reaction in step (a).

7. The method of claim 2, wherein step (a) comprises performing with an automated nucleic acid analyzer that isolates the polynucleotide analyte, and then amplifies the isolated polynucleotide analyte.

8. The method of claim 7, wherein the automated nucleic acid analyzer further detects synthesis of amplification products as the nucleic acid amplification reaction is occurring.

9. The method of claim 2, wherein the measured result indicates a concentration of the polynucleotide analyte in a plasma sample.

10. The method of claim 2, wherein the nucleic acid amplification reaction is an isothermal nucleic acid amplification reaction.

11. The method of claim 10, wherein the isothermal nucleic acid amplification reaction is a transcription-associated nucleic acid amplification reaction.

12. The method of claim 11, wherein the transcription-associated nucleic acid amplification reaction comprises a transcription mediated amplification (TMA) reaction.

13. The method of claim 6, wherein the polynucleotide analyte comprises a segment of a viral genome.

14. The method of claim 13, wherein the viral genome comprises RNA.

15. The method of claim 14, wherein the polynucleotide analyte comprises a segment of an HIV-1 genome.

16. The method of claim 2, wherein the fluid blood sample comprises whole blood.

17. A method of quantifying an analyte present in a bodily fluid sample that dried to produce a dried sample, the method comprising the steps of:
  (a) performing a reaction using the dried sample as a source of analyte to obtain a A measured result, the measured result indicating a concentration or an amount of the analyte;
  (b) multiplying the measured result by a correction factor to obtain a corrected result,
    wherein the correction factor is the solution to an equation that specifies the correction factor as a function of the measured result, and
    wherein the equation comprises a non-linear equation, and (c) quantifying the analyte present in the bodily fluid sample and recording the corrected result.

18. The method of claim 17, wherein the non-linear equation comprises coefficients optimized in a mathematical curve fitting procedure to define a fitted curve.

19. The method of claim 18, wherein the non-linear equation comprises four coefficients.

20. The method of claim 17, wherein the analyte is a polynucleotide analyte, and wherein step (a) comprises performing with an automated nucleic acid analyzer that amplifies the polynucleotide analyte and detects amplification products as the nucleic acid amplification reaction is occurring.

21. The method of claim 20, wherein the non-linear equation in step (b) comprises coefficients optimized in a mathematical curve fitting procedure to define a fitted curve, and wherein the non-linear equation is prepared using results obtained from an automated nucleic acid analyzer different from the automated nucleic acid analyzer used for performing the nucleic acid amplification reaction in step (a).

22. The method of claim 20, wherein step (a) comprises performing with an automated nucleic acid analyzer that isolates the polynucleotide analyte, and then amplifies the isolated polynucleotide analyte.

23. The method of claim 22, wherein the measured result indicates a concentration of the polynucleotide analyte in a plasma sample.

24. The method of claim 22, wherein the nucleic acid amplification reaction is an isothermal nucleic acid amplification reaction.

25. The method of claim 24, wherein the isothermal nucleic acid amplification reaction is a transcription-associated nucleic acid amplification reaction.

26. The method of claim 25, wherein the transcription-associated nucleic acid amplification reaction comprises a transcription mediated amplification (TMA) reaction.

27. The method of claim 20, wherein the polynucleotide analyte comprises a segment of a viral genome.

28. The method of claim 27, wherein the viral genome comprises RNA.

29. The method of claim 28, wherein the polynucleotide analyte comprises a segment of an HIV-1 genome.

30. The method of claim 17, wherein the bodily fluid sample is selected from the group consisting of a whole blood sample, a plasma sample, a urine sample, and a saliva sample.

* * * * *

UNITED STATES PATENT AND TRADEMARK OFFICE
CERTIFICATE OF CORRECTION

PATENT NO. : 12,195,793 B2
APPLICATION NO. : 18/733583
DATED : January 14, 2025
INVENTOR(S) : Sangeetha Vijaysri Nair et al.

It is certified that error appears in the above-identified patent and that said Letters Patent is hereby corrected as shown below:

In the Specification

In Column 1, Line 10, delete "2022," and insert -- 2022, now U.S. Pat. No. 12,037,638, --, therefor.

In Column 7, Line 61, delete "amount" and insert -- amount of --, therefor.

In Column 11, Line 59, delete "a" and insert -- as a --, therefor.

In Column 19, Line 25, delete "recommended" and insert -- recommended as --, therefor.

In Column 19, Line 44, delete "$\sqrt{(Bias)^2+(StdDev)^2} \leq 1 \log$" and insert -- $\sqrt{(Bias)^2 + (Std\ Dev)^2} \leq 1 \log$ --, therefor.

In the Claims

In Column 26, Line 18, in Claim 1, delete "result A" and insert -- result --, therefor.

In Column 27, Line 25, in Claim 17, delete "a A" and insert -- a --, therefor.

Signed and Sealed this
Sixteenth Day of September, 2025

Coke Morgan Stewart
*Acting Director of the United States Patent and Trademark Office*